United States Patent
Bruchman et al.

(10) Patent No.: US 9,744,033 B2
(45) Date of Patent: Aug. 29, 2017

(54) ELASTOMERIC LEAFLET FOR PROSTHETIC HEART VALVES

(71) Applicant: W. L. Gore & Associates, Inc., Newark, DE (US)

(72) Inventors: William C. Bruchman, Camp Verde, AZ (US); Charles F. White, Tonto Basin, AZ (US)

(73) Assignee: W.L. GORE & ASSOCIATES, Inc., Newark, DE (US)

( * ) Notice: Subject to any disclaimer, the term of this patent is extended or adjusted under 35 U.S.C. 154(b) by 280 days.

(21) Appl. No.: 14/181,965

(22) Filed: Feb. 17, 2014

(65) Prior Publication Data

US 2014/0180402 A1  Jun. 26, 2014

Related U.S. Application Data

(63) Continuation-in-part of application No. 13/485,823, filed on May 31, 2012, now Pat. No. 8,945,212, and
(Continued)

(51) Int. Cl.
*A61F 2/24* (2006.01)
*A61L 27/34* (2006.01)
(Continued)

(52) U.S. Cl.
CPC .......... *A61F 2/2418* (2013.01); *A61F 2/2415* (2013.01); *A61L 27/34* (2013.01);
(Continued)

(58) Field of Classification Search
None
See application file for complete search history.

(56) References Cited

U.S. PATENT DOCUMENTS

| | | |
|---|---|---|
| 3,953,566 A | 4/1976 | Gore |
| 4,339,831 A | 7/1982 | Johnson |
| 4,340,091 A | 7/1982 | Skelton et al. |
| 4,629,459 A | 12/1986 | Ionescu et al. |
| 4,877,661 A | 10/1989 | House et al. |
| 4,955,899 A * | 9/1990 | Della Corna ............. A61F 2/06 427/2.25 |
| 5,026,513 A | 6/1991 | House et al. |
| 5,071,609 A | 12/1991 | Tu et al. |
| 5,476,589 A | 12/1995 | Bacino |
| 5,534,007 A | 7/1996 | St. Germain et al. |
| 5,549,663 A | 8/1996 | Cottone |
| 5,708,044 A | 1/1998 | Branca |

(Continued)

FOREIGN PATENT DOCUMENTS

| | | |
|---|---|---|
| EP | 150608 | 8/1985 |
| EP | 313263 | 10/1988 |

(Continued)

OTHER PUBLICATIONS

International Search Report and Written Opinion for PCT/US2015/042530 dated Oct. 6, 2015, corresponding to U.S. Appl. No. 14/622,599, 3 pages.

(Continued)

*Primary Examiner* — Brian Pellegrino
*Assistant Examiner* — Wade P Schutte

(57) ABSTRACT

A leaflet for a prosthetic valve formed of at least one layer that includes a composite material containing at least one expanded fluoropolymer membrane having serpentine fibrils and an elastomer is provided. The fluoropolymer may be polytetrafluoroethylene. In at least one embodiment, the elastic properties are present in an axial direction the leaflet. The leaflets may be single layered or multi-layered. The leaflets may be coupled to a support structure and movable between open and closed configurations relative to the support structure to form a heart valve. The elasticity within the leaflets permits, among other things, the leaflets to bend with a reduced occurrence of wrinkles as the valve opens and closes. The elastic properties of the leaflet also, among other things, improve bending properties and reduce closure stresses, thereby extending the life of the leaflet.

52 Claims, 9 Drawing Sheets

Related U.S. Application Data a continuation-in-part of application No. 13/485,823, filed on May 31, 2012, now Pat. No. 8,945,212, which is a continuation-in-part of application No. 13/078,774, filed on Apr. 1, 2011, now Pat. No. 8,961,599, application No. 14/181,965, which is a continuation-in-part of application No. 13/078,774.

(51) Int. Cl.
  *A61L 27/48* (2006.01)
  *A61L 27/56* (2006.01)

(52) U.S. Cl.
  CPC .............. *A61L 27/48* (2013.01); *A61L 27/56* (2013.01); *A61F 2210/0076* (2013.01); *A61L 2420/04* (2013.01); *A61L 2420/08* (2013.01); *A61L 2430/20* (2013.01)

(56) References Cited

U.S. PATENT DOCUMENTS

| | | |
|---|---|---|
| 5,718,973 A | 2/1998 | Lewis et al. |
| 5,759,192 A | 6/1998 | Saunders |
| 5,769,884 A | 6/1998 | Solovay |
| 5,772,884 A | 6/1998 | Tanaka et al. |
| 5,824,043 A | 10/1998 | Cottone |
| 5,843,158 A | 12/1998 | Lenker et al. |
| 5,843,161 A | 12/1998 | Solovay |
| 5,935,162 A | 8/1999 | Dang |
| 6,010,529 A | 1/2000 | Herweck et al. |
| 6,013,854 A | 1/2000 | Moriuchi |
| 6,042,588 A | 3/2000 | Munsinger et al. |
| 6,042,606 A | 3/2000 | Frantzen |
| 6,190,406 B1 | 2/2001 | Duerig et al. |
| 6,245,012 B1 | 6/2001 | Kleshinski |
| 6,261,320 B1 | 7/2001 | Tam et al. |
| 6,436,132 B1 | 8/2002 | Patel et al. |
| 6,451,396 B1 | 9/2002 | Zumbrum |
| 6,488,701 B1 | 12/2002 | Nolting et al. |
| 6,541,589 B1 | 4/2003 | Baillie |
| 6,620,190 B1 | 9/2003 | Colone |
| 6,626,939 B1 | 9/2003 | Burnside et al. |
| 6,673,455 B2 | 1/2004 | Zumbrum |
| 6,730,120 B2 | 5/2004 | Berg et al. |
| 6,755,856 B2 | 6/2004 | Fierens et al. |
| 6,758,858 B2 | 7/2004 | McCrea et al. |
| 6,770,579 B1 | 8/2004 | Dawson |
| 6,776,604 B1 | 8/2004 | Chobotov et al. |
| 7,049,380 B1 | 5/2006 | Chang et al. |
| 7,083,642 B2 | 8/2006 | Sirhan et al. |
| 7,105,018 B1 | 9/2006 | Yip et al. |
| 7,306,729 B2 | 12/2007 | Bacino |
| 7,419,678 B2 | 9/2008 | Falotico |
| 7,448,122 B1* | 11/2008 | Kokish .................. A61F 2/958 29/446 |
| 7,462,675 B2 | 12/2008 | Chang et al. |
| 7,531,611 B2 | 5/2009 | Sabol et al. |
| 7,628,803 B2 | 12/2009 | Pavcnik et al. |
| 7,789,908 B2 | 9/2010 | Sowinski et al. |
| 7,811,314 B2 | 10/2010 | Fierens et al. |
| 7,815,763 B2 | 10/2010 | Fierens et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 8,637,144 B2 | 1/2014 | Ford |
| 2001/0051824 A1 | 12/2001 | Hopkins |
| 2002/0198588 A1 | 12/2002 | Armstrong et al. |
| 2003/0004559 A1 | 1/2003 | Lentz et al. |
| 2003/0055492 A1 | 3/2003 | Shaolian et al. |
| 2003/0055495 A1 | 3/2003 | Pease et al. |
| 2003/0060871 A1 | 3/2003 | Hill et al. |
| 2003/0211264 A1 | 11/2003 | Farnsworth et al. |
| 2004/0019374 A1 | 1/2004 | Hojeibane et al. |
| 2004/0024448 A1 | 2/2004 | Chang |
| 2004/0093070 A1 | 5/2004 | Hojeibane et al. |
| 2005/0080476 A1 | 4/2005 | Gunderson et al. |
| 2005/0137682 A1 | 6/2005 | Justino |
| 2005/0283224 A1 | 12/2005 | King |
| 2006/0036311 A1 | 2/2006 | Nakayama et al. |
| 2006/0058889 A1 | 3/2006 | Case et al. |
| 2006/0259133 A1 | 11/2006 | Sowinski et al. |
| 2006/0276883 A1 | 12/2006 | Greenberg et al. |
| 2007/0012624 A1 | 1/2007 | Bacino et al. |
| 2007/0027535 A1* | 2/2007 | Purdy, Jr. .............. A61F 2/2412 623/2.18 |
| 2007/0060999 A1 | 3/2007 | Randall et al. |
| 2007/0118210 A1 | 5/2007 | Pinchuk |
| 2007/0129786 A1 | 6/2007 | Beach et al. |
| 2007/0208421 A1 | 9/2007 | Quigley |
| 2007/0213800 A1 | 9/2007 | Fierens et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2007/0288087 A1 | 12/2007 | Fearnot et al. |
| 2008/0051876 A1 | 2/2008 | Ta et al. |
| 2008/0091261 A1 | 4/2008 | Long et al. |
| 2008/0119943 A1 | 5/2008 | Armstrong et al. |
| 2008/0125711 A1 | 5/2008 | Alpini et al. |
| 2008/0133004 A1 | 6/2008 | White |
| 2008/0319531 A1 | 12/2008 | Doran et al. |
| 2009/0004239 A1 | 1/2009 | Ladet |
| 2009/0005854 A1 | 1/2009 | Huang et al. |
| 2009/0030499 A1 | 1/2009 | Bebb et al. |
| 2009/0043373 A1 | 2/2009 | Arnault de la Menardiere et al. |
| 2009/0182413 A1 | 7/2009 | Burkart et al. |
| 2009/0187197 A1 | 7/2009 | Roeber |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0159171 A1 | 6/2010 | Cough |
| 2010/0190254 A1 | 7/2010 | Chian |
| 2010/0248324 A1 | 9/2010 | Xu et al. |
| 2010/0249922 A1 | 9/2010 | Li |
| 2011/0039690 A1 | 2/2011 | Niu |
| 2011/0142804 A1 | 6/2011 | Gaudette |
| 2011/0250689 A1 | 10/2011 | Baaijens |
| 2011/0311746 A1 | 12/2011 | Ma |
| 2012/0058100 A1 | 3/2012 | Shastri |
| 2012/0061314 A1 | 3/2012 | Choi |
| 2012/0129150 A1 | 5/2012 | Carbonell |
| 2012/0253453 A1 | 10/2012 | Bruchman et al. |
| 2012/0290082 A1 | 11/2012 | Quint et al. |
| 2012/0296418 A1 | 11/2012 | Bonyuet |
| 2012/0323211 A1 | 12/2012 | Ogle |
| 2012/0323315 A1 | 12/2012 | Bruchman et al. |
| 2013/0150947 A1 | 6/2013 | Kaufmann |
| 2013/0184807 A1 | 7/2013 | Kovach et al. |
| 2013/0310924 A1 | 11/2013 | Groothuis |
| 2014/0135897 A1 | 5/2014 | Cully et al. |
| 2014/0172066 A1 | 6/2014 | Goepfrich et al. |
| 2014/0180400 A1 | 6/2014 | Bruchman et al. |
| 2014/0180402 A1 | 6/2014 | Bruchman et al. |
| 2014/0288642 A1 | 9/2014 | Yoshida |
| 2015/0224231 A1 | 8/2015 | Bruchman |
| 2015/0257876 A1 | 9/2015 | Bruchman |
| 2015/0265744 A1 | 9/2015 | Baaijens |
| 2015/0283297 A1 | 10/2015 | Baaijens |
| 2015/0305862 A1 | 10/2015 | Bruchman |
| 2015/0306277 A1 | 10/2015 | Pathak |
| 2015/0366663 A1 | 12/2015 | Bruchman |
| 2016/0008133 A9 | 1/2016 | Day |
| 2016/0067374 A1 | 3/2016 | Puckett |

FOREIGN PATENT DOCUMENTS

| | | |
|---|---|---|
| EP | 293090 | 11/1988 |
| EP | 0 815 806 | 1/1997 |
| EP | 773971 | 5/1997 |
| EP | 0 893 108 | 1/1999 |
| EP | 1 977 719 | 10/2008 |
| JP | H02-645 | 1/1990 |
| JP | H09-501759 | 2/1997 |
| JP | H09-241412 | 9/1997 |

(56) References Cited

FOREIGN PATENT DOCUMENTS

| | | |
|---|---|---|
| JP | H11-290448 | 10/1999 |
| JP | 2005-530549 | 10/2005 |
| JP | 2008-506459 | 3/2008 |
| JP | 2010/535075 | 11/2010 |
| RU | 2124986 | 8/1994 |
| WO | 95/05555 | 2/1995 |
| WO | 95/28899 | 11/1995 |
| WO | 97/10871 | 3/1997 |
| WO | 98/26731 | 6/1998 |
| WO | 00/41649 | 7/2000 |
| WO | 01/74272 | 10/2001 |
| WO | 02/060506 | 8/2002 |
| WO | 02/100454 | 12/2002 |
| WO | 04/000375 | 12/2003 |
| WO | 2006/000763 | 1/2006 |
| WO | 2006/019626 | 2/2006 |
| WO | 2007/002320 | 1/2007 |
| WO | 2007/016251 | 2/2007 |
| WO | 2008/028964 | 3/2008 |
| WO | 2008/036870 | 3/2008 |
| WO | 2008/049045 | 4/2008 |
| WO | 2009/017827 | 2/2009 |
| WO | 2009/038761 | 3/2009 |
| WO | 2009/100210 | 8/2009 |
| WO | 2009/149462 | 12/2009 |
| WO | 2010/006783 | 1/2010 |
| WO | 2010/030766 | 3/2010 |
| WO | 2010/132707 | 11/2010 |
| WO | 2011/065809 | 6/2011 |

OTHER PUBLICATIONS

International Search Report and Written Opinion for PCT/US2011/061165 dated Oct. 1, 2012, corresponding to U.S. Appl. No. 13/298,060.
International Search Report and Written Opinion for PCT/US2012/064910 dated Feb. 1, 2013, corresponding to U.S. Appl. No. 13/675,764, 8 pages.
International Search Report and Written Opinion for PCT/US2012/064908 dated Feb. 4, 2013, corresponding to U.S. Appl. No. 13/675,730, 11 pages.
International Search Report and Written Opinion for PCT/US2012/066518, dated Feb. 4, 2013, corresponding to U.S. Appl. No. 13/351,052, 12 pages.
Partial International Search Report for PCT/US2012/065066, dated Jul. 1, 2013, corresponding to U.S. Appl. No. 13/675,959, 3 pages.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.
International Search Report for PCT/US2012/065066, dated Nov. 11, 2013, corresponding to U.S. Appl. No. 13/675,959, 10 pages.
Google Image Search Results, "S-Shaped", accessed Nov. 1, 2013.
International Search Report and Written Opinion for PCT/US2012/031417 dated Oct. 18, 2012, corresponding to U.S. Appl. No. 13/078,774.
International Search Report and Written Opinion for PCT/US2012/040529 dated Nov. 14, 2012 corresponding to U.S. Appl. No. 13/485,823.
Annex to Form PCT/ISA/206 Communication Relating to the Results of the Partial International Search PCT/US2014/016550 dated Apr. 8, 2014, corresponding to U.S. Appl. No. 13/798,595; 3 pages.
International Search Report and Written Opinion for PCT/US2014/016581 dated Apr. 8, 2014, corresponding to U.S. Appl. No. 13/801,701; 4 pages.
International Search Report and Written Opinion for PCT/US2014/016550 dated Jul. 2, 2014, corresponding to U.S. Appl. No. 13/798,595; 9 pages.
International Search Report and Written Opinion for PCT/US2014/016807 dated May 30, 2014, corresponding to U.S. Appl. No. 14/181,965, 4 pages.

* cited by examiner

ELASTOMERIC LEAFLET FOR PROSTHETIC HEART VALVES

FIELD

The subject matter disclosed herein relates to materials used in medical implants, and more particularly, to a leaflet that includes at least one layer of a composite material that includes an expanded polytetrafluoroethylene (ePTFE) membrane containing serpentine fibrils and an elastomer. The elastomer may be located in all or substantially all of the pores of the ePTFE membrane.

BACKGROUND

Artificial heart valves desirably last at least ten years in vivo. To last that long, artificial heart valves should exhibit sufficient durability for at least four hundred million cycles or more. The valves, and more specifically heart valve leaflets, must resist structural degradation including the formation of holes, tears, and the like as well as adverse biological consequences such as calcification and thrombosis.

Fluoropolymers, such as expanded and non-expanded forms of polytetrafluoroethylene (PTFE), modified PTFE, and copolymers of PTFE, offer a number of desirable properties, including excellent inertness and superior biocompatibility, and therefore make ideal candidate materials for artificial heart valves. Additionally, PTFE and expanded PTFE (ePTFE) have been used to create heart valve leaflets. It has been shown, however, that PTFE stiffens with repeated flexure, which can lead to unacceptable flow performance. Failure due to formation of holes and tears in the material has also been observed. A variety of polymeric materials has previously been employed as prosthetic heart valve leaflets. Failure of these polymeric leaflets due to stiffening and hole formation typically occurred within two years of implant. Efforts to improve leaflet durability by thickening the leaflets resulted in unacceptable hemodynamic performance of the valves, that is, the pressure drop across the open valve was too high. Conventional leaflets also experience wrinkling, which can be sites of potential failure of the heart valve.

Thus, there remains a need in the art for a biocompatible artificial heart valve, including leaflets, that is durable and reduces the occurrence of wrinkles during the cycling of the heart valve between open and closed configurations.

SUMMARY

According to an embodiment, a prosthetic valve is provided for regulating blood flow direction in a human patient. Such a prosthetic valve includes, but is not limited to, a cardiac valve or a venous valve.

Embodiments provided herein utilize fluoropolymer membranes that exhibit significant elongation while substantially retaining the strength properties of the fluoropolymer membrane. Such fluoropolymer membranes characteristically possess serpentine fibrils.

Other embodiments provide a prosthetic valve for regulating blood flow direction within a patient that includes a leaflet having at least one layer of a composite material that contains at least one expanded fluoropolymer membrane having serpentine fibrils and an elastomer. In embodiments, the elastomer is present in all or substantially all of the pores of the fluoropolymer membrane. The fluoropolymer membrane may have a microstructure of substantially only serpentine fibrils. In some embodiments, the expanded fluoropolymer membrane includes a plurality of serpentine fibrils. In addition, the fluoropolymer may be polytetrafluoroethylene. The leaflet may be formed of a single layer or multiple layers of the composite material. Additionally, the leaflets may be operatively connected to a support structure and movable between open and closed configurations relative to the support structure to form a heart valve. The elasticity within the leaflets permits the leaflets to bend with a reduced occurrence of wrinkling as the valve opens and closes. Leaflets formed of the composite material exhibit no visible signs of holes, tears, or delamination and remain otherwise unchanged after actuation of the leaflet for at least 100 million cycles.

Other embodiments provide an implantable prosthetic valve for regulating blood flow direction in a patient that includes a leaflet cyclable between a closed configuration to substantially prevent blood flow through the prosthetic valve and an open configuration to allow blood flow through the prosthetic valve. The leaflet is formed of at least one layer of a composite material that includes at least one expanded fluoropolymer membrane having serpentine fibrils and an elastomer. The elastomer is present in all or substantially all of the pores of the expanded fluoropolymer membrane. In addition, the expanded fluoropolymer membrane may include a microstructure of substantially only serpentine fibrils. The expanded fluoropolymer membrane may include a plurality of serpentine fibrils. In some embodiments, the fluoropolymer is polytetrafluoroethylene. The leaflet has a reduced occurrence of wrinkling in the open and closed configurations of the prosthetic valve. Additionally, the leaflet may be may be coupled to a rigid or an elastic support structure in a conventional manner to form a heart valve.

Embodiments provided herein provide a method of forming a leaflet of an implantable prosthetic valve for regulating blood flow direction in a patient that includes providing a composite material that includes at least one expanded fluoropolymer membrane having serpentine fibrils and an elastomer and bringing at least one layer of the composite material into contact with additional layers of the composite material by wrapping a sheet of the composite material with a starting and ending point defined as an axial seam adhered to itself. The elastomer may be present in all or substantially all of the pores of the expanded fluoropolymer membrane. In accordance with an embodiment, the elastic properties of the leaflet are present in the axial direction of the leaflet. The fluoropolymer may be polytetrafluoroethylene. Also, the expanded fluoropolymer membrane may include a microstructure of substantially only serpentine fibrils. In accordance with another embodiment, the expanded fluoropolymer membrane includes a plurality of serpentine fibrils.

Other embodiments provide an implantable prosthetic valve for regulating blood flow direction in a patient that includes a support structure and a leaflet formed of at least one layer that includes a composite material containing at least one expanded fluoropolymer membrane having serpentine fibrils and an elastomer. The expanded fluoropolymer membrane includes a plurality of pores and the elastomer is present in all or substantially all of the pores. Additionally, the leaflet is movable relative to the support structure and is cyclable between a closed configuration and an open configuration. The leaflet has a reduced occurrence of wrinkling in both the open and closed configurations. In some embodiments, the fluoropolymer is polytetrafluoroethylene. The expanded fluoropolymer membrane may include a microstructure of substantially only serpentine fibrils. The expanded fluoropolymer membrane may include a plurality of serpentine fibrils.

Other embodiments provide an prosthetic valve that includes a leaflet having at least one layer comprising a composite material that exhibits an increase in stiffness when elongated to at least about 30% strain. The composite material includes at least one expanded fluoropolymer membrane and an elastomer. The expanded fluoropolymer membrane may include serpentine fibrils. Also, the expanded fluoropolymer membrane may include a plurality of serpentine fibrils. In an embodiment, the expanded fluoropolymer membrane includes a plurality of pores and the elastomer is present in substantially all of the pores.

An embodiment of a method of forming a leaflet includes providing a composite material that exhibits an increase in stiffness when elongated to at least about 30% strain and bringing at least one layer of the composite material into contact with additional layers of the composite material by wrapping a sheet of the composite material with a starting and ending point defined as an axial seam adhered to itself. The composite material includes at least one expanded fluoropolymer membrane and an elastomer, and, in some embodiments, may include serpentine fibrils.

Leaflets formed with the composite material may be operatively coupled to a support structure and movable between closed and open configurations relative to the support structure to form a heart valve.

Leaflets in accordance with embodiments provided herein demonstrate a reduction of wrinkling as the heart valves cycle between an open configuration and a closed configuration.

Embodiments provided herein provide that the elastomer may be present in all or substantially all of the pores of the fluoropolymer membrane.

Other embodiments provide that additional materials may be incorporated into the pores of the expanded fluoropolymer membrane or between the layers of the composite material forming the leaflet to enhance desired properties of the leaflet.

DETAILED DESCRIPTION OF THE INVENTION

Figure 1:
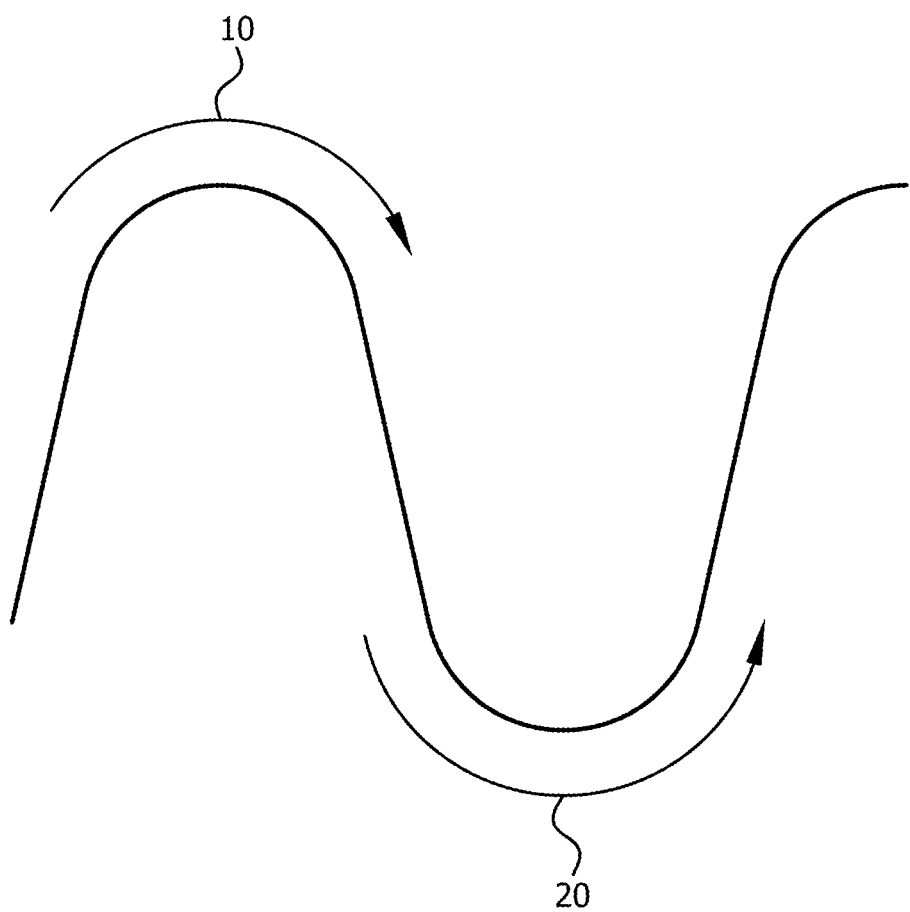
FIG. 1 is a schematic illustration of an exemplary, idealized serpentine fibril, in accordance with an embodiment.

References will now be made to embodiments illustrated in the drawings and specific language which will be used to describe the same. It will nevertheless be understood that no limitation of the scope of the invention is thereby intended, such alterations and further modifications in the illustrated methods and apparatus, as such further applications of the principles of the invention as illustrated therein as being contemplated as would normally occur to one skilled in the art to which the invention relates.

Unless defined otherwise, all technical and scientific terms used herein have the same meaning as commonly understood by one of ordinary skill in the art to which the invention belongs. In the drawings, the thickness of the lines, layers, and regions may be exaggerated for clarity. Like numbers found throughout the figures denote like elements.

As used herein, the term "serpentine fibrils" means multiple fibrils that curve or turn one way then another.

As used herein, the term "controlled retraction" refers to causing articles to shorten in length in at least one direction by the application of heat, by wetting with a solvent, or by any other suitable means or combinations thereof in such a way as to inhibit folding, pleating, or wrinkling of the subsequent article visible to the naked eye.

The term "wrinkling" also refers to the appearance of the composite material upon bending or flexing of the otherwise wrinkle-free composite material forming the leaflet.

As used herein, the term "wrinkle-free" is meant to denote that the composite material is free of wrinkles prior to bending or flexing the composite material.

The term "imbibed or imbibing" as used herein is meant to describe any means for at least partially filling at least a portion of the pores of a porous material such as ePTFE or the like.

The term "elongation" or "elongated" as used herein is meant to denote the increase in length in response to the application of a force.

The term "leaflet" as used herein is meant to denote a component of a prosthetic valve for regulating blood flow direction. Leaflets according to the present embodiments are formed of one or more layers of a composite material including an expanded fluoropolymer membrane having serpentine fibrils and an elastomer.

The term "elastic" as used herein refers to the property of a material to be elongated upon the application of a force and that returns to its approximate original dimensions upon the release of the force due to the retraction force of the material.

The term "increase in stiffness" as used herein refers the increase in resistance to further elongation once the stop-point is reached.

The terms "node" and "fibril" as used herein refers to particular characteristic shapes of elements of the structure of an expanded fluoropolymer membrane, as is known in the art of expanded fluoropolymer membranes.

In one embodiment, fluoropolymer membranes that exhibit high elongation while substantially retaining the strength properties of the fluoropolymer membrane are utilized. Such membranes characteristically possess serpentine fibrils, such as the idealized serpentine fibril exemplified in FIG. 1. As depicted generally in FIG. 1, a serpentine fibril curves or turns generally one way in the direction of first arrow 10 then generally another way in the direction of second arrow 20. It is to be understood that the amplitude, frequency, or periodicity of the serpentine-like fibrils as exemplified in FIG. 1 may vary. In one embodiment, the fluoropolymer membranes are expanded fluoropolymer membranes. Non-limiting examples of expandable fluoropolymers include, but are not limited to, expanded PTFE, expanded modified PTFE, and expanded copolymers of PTFE. Patents have been filed on expandable blends of PTFE, expandable modified PTFE, and expanded copolymers of PTFE, such as, for example, U.S. Pat. No. 5,708,044 to Branca; U.S. Pat. No. 6,541,589 to Baillie; U.S. Pat. No. 7,531,611 to Sabol et al.; U.S. patent application Ser. No. 11/906,877 to Ford; and U.S. patent application Ser. No. 12/410,050 to Xu et al.

The high elongation is enabled by forming relatively straight fibrils into serpentine fibrils that substantially straighten upon the application of a force in a direction opposite to the compressed direction. The creation of the serpentine fibrils can be achieved through a thermally-induced controlled retraction of the expanded polytetrafluoroethylene (ePTFE), through wetting the article with a solvent, such as, but not limited to, isopropyl alcohol or Fluorinert® (a perfluorinated solvent commercially available from 3M, Inc., St. Paul, Minn.), or by a combination of these two techniques. The retraction of the article does not result in visible pleating, folding, or wrinkling of the ePTFE, unlike what occurs during mechanical compression. The retraction also can be applied to very thin membranes, unlike known methods. During the retraction process, the fibrils not only become serpentine in shape but also may also increase in width.

The precursor materials can be biaxially expanded ePTFE membranes. In one embodiment, materials such as those made in accordance with the general teachings of U.S. Pat. No. 7,306,729 to Bacino, et al. are suitable precursor membranes, especially if small pore size articles are desired. These membranes may possess a microstructure of substantially only fibrils. The precursor membrane may or may not be amorphously locked. The precursor membrane may also be at least partially filled, coated, imbibed, or otherwise combined with additional materials (e.g., elastomeric materials).

The precursor membrane may be restrained in one or more directions during the retraction process in order to prescribe the desired amount of elongation of the final article. The amount of elongation is directly related to, and determined by, the amount of retraction.

In one embodiment, retraction can be achieved in a uniaxial tenter frame by positioning the rails at a distance less than the width of the precursor membrane prior to the application of heat or solvent or both. When using a biaxial tenter frame, one or both of the sets of grips, pins, or other suitable attachment means can similarly be positioned at a distance less than the dimensions of the precursor membrane. It is to be appreciated that these retraction means differ from the mechanical compression taught by the House and Sowinski patents noted above. Upon retraction, the expanded fluoropolymer membrane possesses serpentine fibrils. These retracted membranes characteristically possess serpentine fibrils and are substantially wrinkle free. In some exemplary embodiments, the retracted membranes may possess a microstructure of substantially only serpentine fibrils. In at least one embodiment, the fluoropolymer membranes include a plurality of serpentine fibrils. As used herein, the phrase "plurality of serpentine fibrils" is meant to denote the presence of 2 or more, 5 or more, 10 or more, or 15 or more serpentine fibrils in the fluoropolymer membrane within a field of view as taught below.

At least one elastomeric material can be added to the precursor membrane prior, during, or subsequent to retraction to form a composite. In the absence of such elastomeric materials, fluoropolymer articles having serpentine fibrils do not exhibit appreciable recovery after elongation. Suitable elastomeric materials may include, but are not limited to, PMVE-TFE (perfluoromethylvinyl ether-tetrafluoroethylene) copolymers, PAVE-TFE (perfluoro (alkyl vinyl ether)-tetrafluoroethylene) copolymers, silicones, polyurethanes, and the like. It is to be noted that PMVE-TFE and PAVE-TFE are fluoroelastomers. Other fluoroelastomers are suitable elastomeric materials. The resultant retracted article not only possesses high elongation while substantially retaining the strength properties of the fluoropolymer membrane, it also possesses an additional property of low percent unrecoverable strain energy density. These retracted articles can exhibit percent unrecoverable strain energy density values less than about 90%, less than about 85%, less than about 80%, less than about 70%, less than about 60%, and lower, including any and all percentages therebetween.

In one embodiment, a composite material including an expanded fluoropolymer membrane having serpentine fibrils and an elastomer as described above forms the leaflet materials of a heart valve. The composite material is substantially free of wrinkles. It is to be appreciated that the use of a single layer or multiple layers of the expanded fluoropolymer membrane and multiple types of elastomeric materials are considered to be within the scope of the present disclosure. Additional materials may also be incorporated into the pores of the expanded fluoropolymer membrane and/or between layers of the composite material forming the leaflet to enhance desired properties of the leaflet. The fluoropolymer membrane exhibits significant elongation while substantially retaining the strength properties of the fluoropolymer membrane.

The composite material provides performance attributes required for use in high-cycle flexural implant applications, such as heart valve leaflets, in several significant ways. For example, the inclusion of the elastomer improves the fatigue performance of the leaflet by eliminating or reducing stiffening that is typically observed with ePTFE-only materials. In addition, the incorporation of an elastomer reduces the likelihood that the material will undergo permanent set deformation, such as wrinkling or creasing, that could result in compromised performance.

Composite materials of embodiments herein not only exhibit elongation, but also exhibit a dramatic increase in stiffness after achieving a high, optionally predetermined, elongation. As a consequence, the composite materials can be elongated to a point at which further elongation is inhibited by the dramatic increase in stiffness. The composite material has a stop point at which further elongation occurs only in conjunction with a significant increase in pressure or force. The composite material exhibits an increase in stiffness when elongated to at least about 30% strain, to at least about 35% strain, to at least about 40% strain, to at least about 45% strain, to at least about 50% strain, to at least about 55% strain, and even greater.

As discussed above, the elastomer may be combined with the expanded fluoropolymer membrane such that the elastomer occupies all or substantially all of the pores within the expanded fluoropolymer membrane. The term "substantially all of the pores" as used herein is meant to denote that the elastomer is present in at least a portion of all or nearly all of the pores of the expanded fluoropolymer (ePTFE) membrane. Having elastomer present in all or substantially all of the pores of the fluoropolymer membrane reduces the space in which foreign materials can be undesirably incorporated into the composite material. An example of such a foreign material is calcium. For instance, if calcium becomes incorporated into the composite material used in a heart valve leaflet, mechanical damage can occur during cycling, which can lead to the formation of holes in the leaflet and degradation in hemodynamics. On the other hand, the incorporation of additional, desired materials into the pores of the expanded fluoropolymer membrane and/or between layers of the composite material forming the leaflet can enhance desired properties of the leaflet, and are considered to be within the scope of the invention.

Leaflets constructed from the composite material can be assembled in a variety of configurations based on desired laminate or leaflet thickness and number of layers of composite material. Leaflets according to some embodiments may be composed of a single layer of the composite material or multiple layers of the composite material. Multi-layers provide for enhanced durability and increased damage reduction to the leaflet. The maximum number of layers within the leaflet is determined, at least in part, by the desired thickness of the leaflet. The leaflet has a ratio of thickness (μm) to number of layers of composite material of less than about 5. In addition, the leaflets may be affixed to a rigid or an elastic frame in a conventional manner, such as, for example, to form a heart valve.

The elasticity within the leaflet greatly reduces the occurrence of wrinkles as the heart valves cycle between an open configuration and a closed configuration. The elastic properties of the leaflet may be present in the axial direction of the leaflet. By "axial direction of the leaflet", it is meant that the direction from the base of the leaflet to the free edge of the leaflet. In addition, the leaflets may have elastic properties in other, non-axial, direction(s). Thus, leaflets formed with the inventive composite material demonstrate a reduction in wrinkling as they bend and flex with the opening and closing of a heart valve. In addition, the elasticity of the leaflet slows accelerations and reduces the forces imposed on the leaflet, thereby extending the life of the leaflet. Leaflets formed of the composite material exhibit no visible signs of holes, tears, or delamination and have unchanged performance after actuation of the leaflet to at least 100 million cycles, and even to at least 200 million cycles.

Additionally, the elastic properties of the leaflet improve bending properties and reduce closure stresses. Bending properties generally refer to the qualitative amount of wrinkles and/or creases developed with in the leaflet structure during deformations induced by cyclic opening and closing.

Having generally described various embodiments, a further understanding can be obtained by reference to certain specific examples illustrated below which are provided for purposes of illustration only and are not intended to be all inclusive or limiting unless otherwise specified.

Testing Methods

It should be understood that although certain methods and equipment are described below, any method or equipment determined suitable by one of ordinary skill in the art may be alternatively utilized.

Mass, Thickness, and Density

Membrane samples were die cut to form rectangular sections about 2.54 cm by about 15.24 cm to measure the weight (using a Mettler-Toledo analytical balance model AG204) and thickness (using a Käfer Fz1000/30 snap gauge). Using these data, density was calculated with the following formula: $\rho=m/(w*l*t)$, in which: $\rho$=density (g/cm$^3$), m=mass (g), w=width (cm), l=length (cm), and t=thickness (cm). The average of three measurements was reported.

Matrix Tensile Strength (MTS) of Membranes

Tensile break load was measured using an INSTRON 122 tensile test machine equipped with flat-faced grips and a 0.445 kN load cell. The gauge length was about 5.08 cm and the cross-head speed was about 50.8 cm/min. The sample dimensions were about 2.54 cm by about 15.24 cm. For highest strength measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness was measured using the Käfer FZ1000/30 snap gauge; alternatively, any suitable means for measuring thickness may be used. The samples were then tested individually on the tensile tester. Three different sections of each sample were measured. The average of the three maximum loads (i.e., peak force) measurements was reported. The longitudinal and transverse matrix tensile strengths (MTS) were calculated using the following equation: MTS=(maximum load/cross-section area)*(bulk density of PTFE)/(density of the porous membrane), where the bulk density of the PTFE was taken to be about 2.2 g/cm$^3$.

Tensile Strength of Composites

Composite tensile testing was performed using an RSA3 dynamic mechanical analyzer (TA Instruments, New Castle, Del.) with a 3500 g load cell. 13 mm×39 mm rectangular samples were mounted with a 20 mm gauge length and strained at a rate of 1000%/minute. For highest strength measurements, the longer dimension of the sample was oriented in the highest strength direction. For the orthogonal tensile strength measurements, the larger dimension of the sample was oriented perpendicular to the highest strength direction. Reported data are an average of at least 3 measurements.

Elongation Testing

Elongation of the retracted article can be measured by any suitable application of tensile force, such as, for example, by the use of a tensile testing machine, by hand, or by applying internal pressure to a tubular article. In the embodiments presented herein, elongation was performed at a rate of about 10% per second in all directions that were elongated. Elongation was calculated as the final length minus the initial length, divided by the initial length, and was reported as a percentage. The average of three measurements was reported.

Percent Unrecoverable Strain Energy Density

Figure 3A:
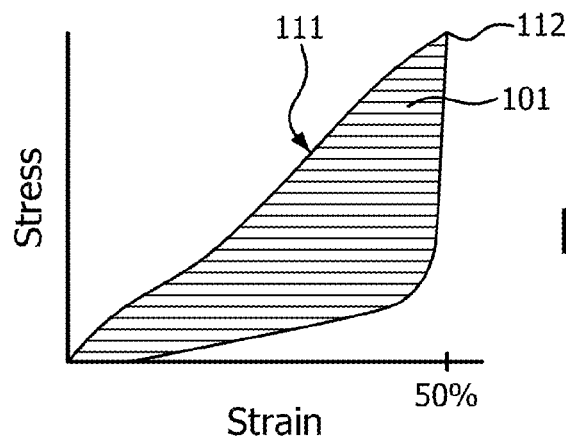
FIG. 3A is a graphical illustration showing the unrecoverable strain energy density of a sample, in accordance with an embodiment.
Figure 3B:
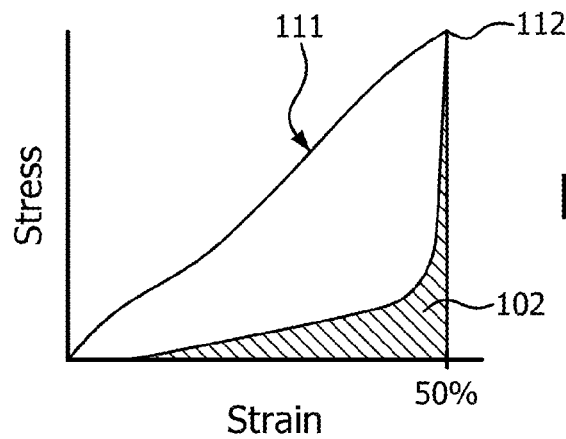
FIG. 3B is a graphical illustration showing the recoverable strain energy density of the sample of FIG. 3A.

The percent unrecoverable strain energy density of composites was measured using an RSA3 dynamic mechanical analyzer (TA Instruments, New Castle, Del.) with a 3500 g load cell. A 13 mm×39 mm rectangular sample was cut so that the longer dimension was oriented in the highest strength direction. The sample was mounted in film/fiber tension grips with a 20 mm gauge length. The grips were programmed to elongate the sample to 50% strain at a rate of 200 mm/minute and were then immediately returned to the initial displacement at a rate of 200 mm/minute. Load and displacement values were collected, converted to stress and strain values, and then graphed. The unrecoverable strain energy density is represented by the first area 101 between the elongation and return curve as depicted in FIG. 3A, shown as hatching. The recoverable strain energy density is represented by the second area 102 in FIG. 3B, shown as hatching.

Figure 3C:
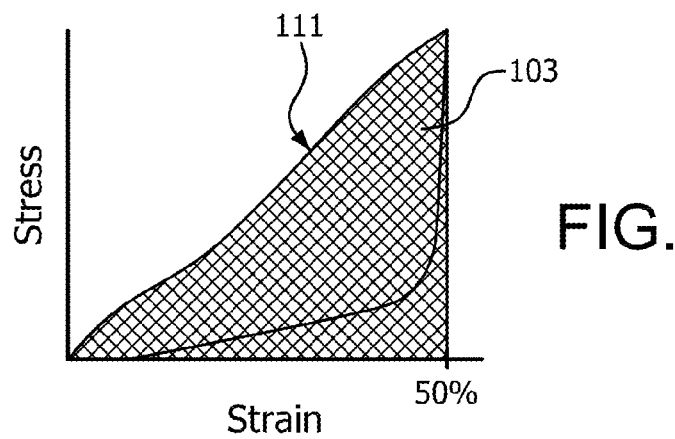
FIG. 3C is a graphical illustration showing the total strain energy density of the sample of FIG. 3A.

The percent unrecoverable strain energy density of the sample is defined by the first area 101 between the elongation and return curve as shown in FIG. 3A, divided by the third area 103 under the elongation curve from 0% to 50% strain as shown in FIG. 3C, shown as crosshatching, then multiplied by 100%. Reported data are an average of at least three measurements.

Should the sample break prior to 50% strain, then another sample should be tested at 50% of the breakage strain to calculate the unrecoverable strain energy density. For samples that are too small to accommodate the 20 mm grip separation and allow enough material within the grips to prevent slippage of the sample within the grips, other combinations of crosshead speed and grip separation may be used provided the ratio of crosshead speed to initial grip separation is equal to 10 minutes.

Scanning Electron Microscopy

Scanning electron micrographs were created choosing magnifications suitable for identifying fibrils. Articles that have been retracted in accordance with the teachings herein may require elongation in the direction of retraction in order to identify the serpentine fibrils. For the purposes of identifying the number of serpentine fibrils, a field of view of 7 microns by 7 microns of the sample is to be employed.

Removal of Elastomer

For porous fluoropolymer leaflets having pores substantially filled with elastomer, the elastomer can be dissolved or degraded and rinsed away using an appropriate solvent in order to measure or examine desired properties.

For instance, the fluoroelastomer component of a leaflet as described in Example 1 can be partially or substantially removed to enable SEM imaging of the ePTFE structure. The sample is restrained from shrinking and submerged in 95 g of Fluorinert Electronic Liquid FC-72 (3M Inc., St. Paul, Minn.) and allowed to soak without agitation. After approximately one hour, the fluorinated solvent is poured off and replaced with 95 g of fresh solvent. This process is repeated for a total of 5 soaking cycles, the first 4 cycles for approximately 1 hour, and the 5th cycle for approximately 24 hours.

To aid in the removal of elastomer, the sample can also be agitated using an ultrasonic cleaner (e.g. Branson 200 Ultrasonic Cleaner (Model-B200)).

Example

Figure 9A:
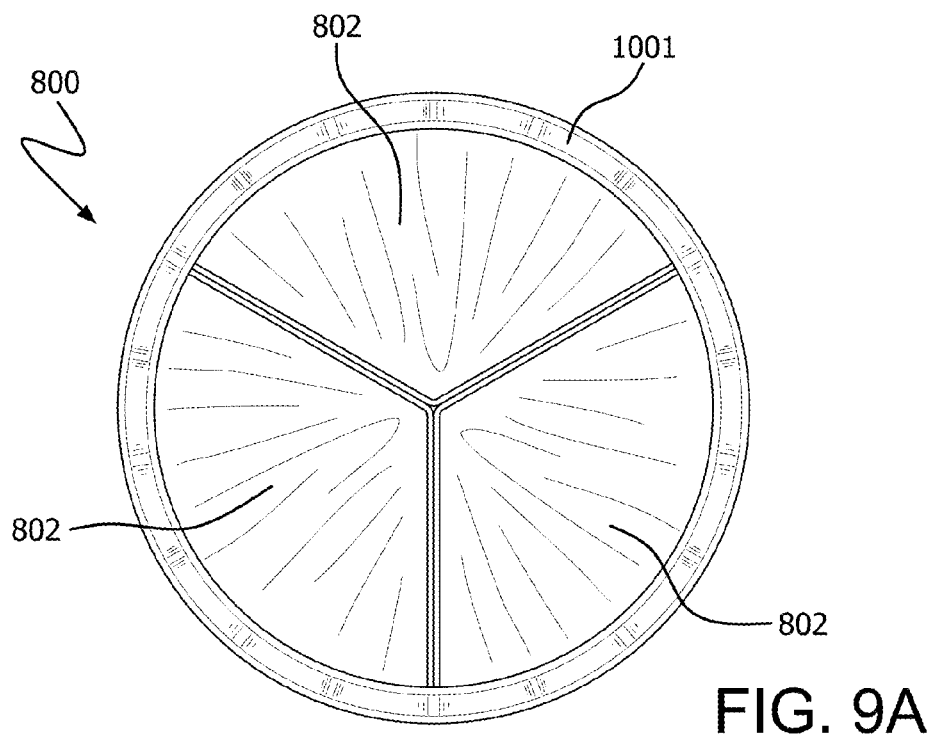
FIGS. 9A and 9B are top views of a valve in the closed and open position, respectively, in accordance with an embodiment.
Figure 9B:
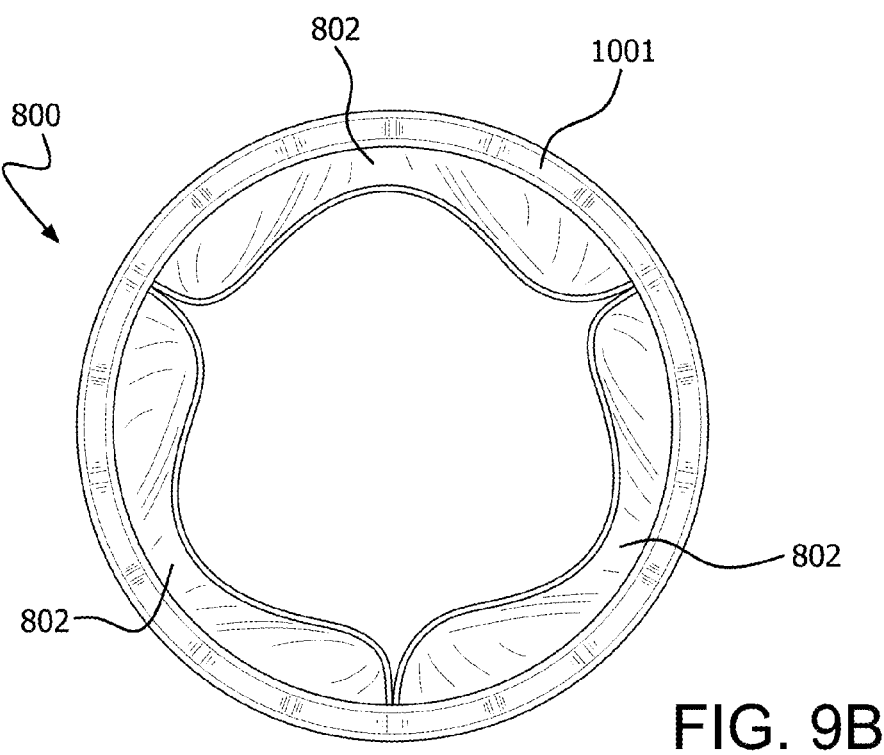

A heart valve having polymeric leaflets was formed from a composite material having an expanded fluoropolymer membrane and an elastomeric material as described above; joined to a metallic balloon expandable support structure; and was constructed according to the following process. FIGS. 9A and 9B are top views of a valve 800 in the closed and open position, respectively, in accordance with an embodiment. The valve 800 comprises a support structure 1001 and three leaflets 802 coupled to the support structure 1001.

Figure 6:
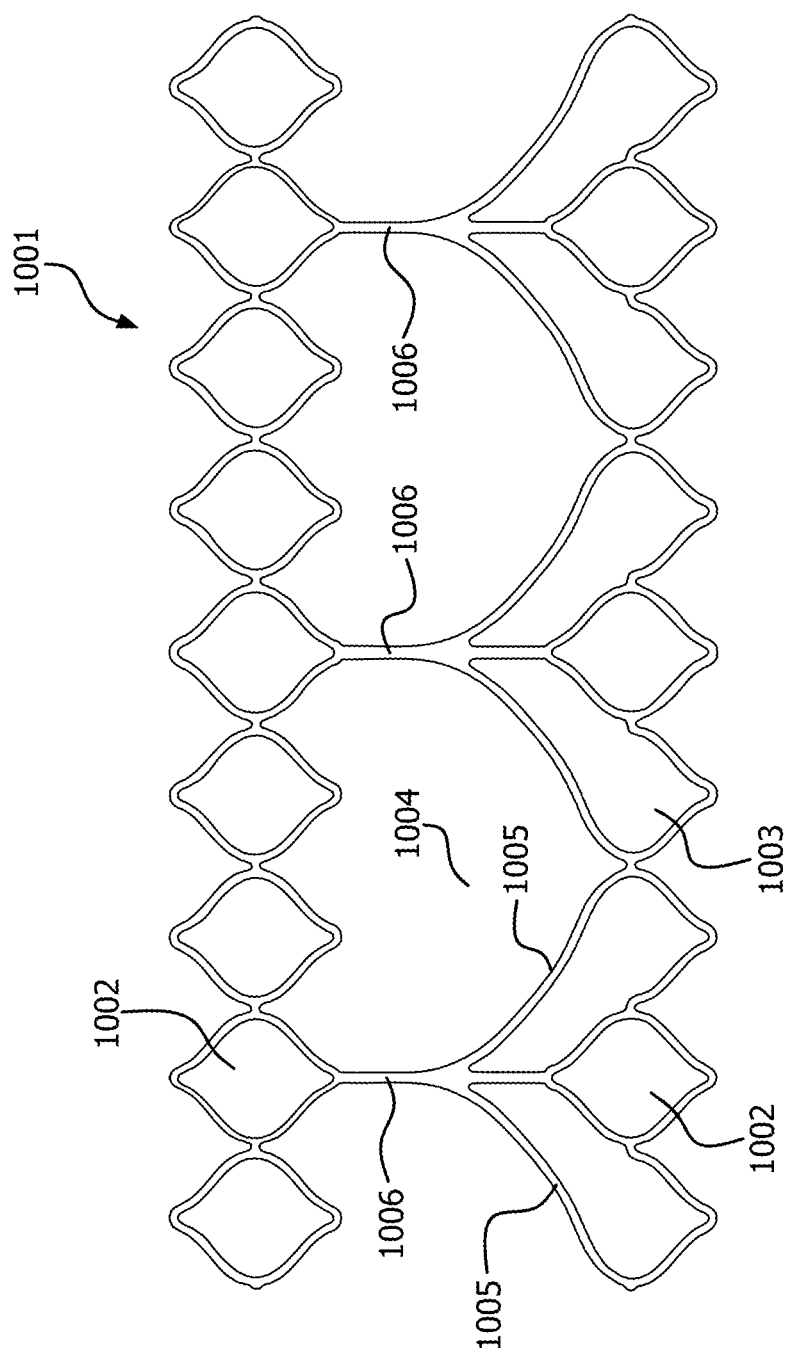
FIG. 6 is a schematic illustration of a cylindrically-shaped cut support structure, in accordance with an embodiment.

A support structure 1001, in the form of a metallic balloon expandable structure, was laser machined from a length of 316LVM stainless steel annealed tube with an outside diameter of 25.4 mm and a wall thickness of 0.502 mm. A pattern was cut into the tube to form a cylindrically-shaped cut stent frame, also referred to as the support structure 1001, as illustrated in the flat plane view of FIG. 6. The support structure 1001 included a plurality of small closed cells 1002, a plurality of large closed cells 1003, and a plurality of leaflet closed cells 1004. It is to be noted that one of the plurality of leaflet closed cells 1004 appears as an open cell in FIG. 6 due to the flat plane view. The small closed cells 1002, large closed cells 1003, and leaflet closed cells 1004 are generally arranged along rows forming the annular shape of the support structure 1001. The support structure 1001 had 6 struts 1005, a portion of which approximates a parabolic shape, as is shown in FIG. 6.

Next, the support structure 1001 was electro-polished, which resulted in 0.025 mm material removal from each surface and left the edges rounded. The corners of support structure 1001 that would be in contact with the leaflet material were rounded using a rotary sander. The support structure 1001 was exposed to a surface roughening step to improve the adherence of leaflets to the support structure 1001, without degrading fatigue durability performance. The support structure 1001 was rinsed with water and then subjected to a plasma cleaning treatment using methods commonly known to those of ordinary skill in the art. The support structure 1001 was dipped into a 4% solution of a fluoroelastomer in PF5080, 3M, St. Paul, Minn., USA and allowed to air dry. The fluoroelastomer was formulated according to the general teachings described in U.S. Pat. No. 7,462,675 to Chang, et al. Additional fluoroelastomers may be suitable and are described in U.S. Publication No. 2004/0024448 to Chang, et al.

The fluoroelastomer consists essentially of between about 65 and 70 weight percent perfluoromethyl vinyl ether and complementally about 35 and 30 weight percent tetrafluoroethylene.

A composite material was then prepared having a membrane layer of biaxially expanded ePTFE imbibed with a fluoroelastomer. More specifically, the membrane layer of ePTFE was manufactured according to the general teachings described in U.S. Pat. No. 7,306,729. The ePTFE membrane was tested in accordance with the methods described previously. The biaxially expanded ePTFE membrane that was not amorphously locked, and had the following properties was used: thickness=0.0025 mm, density=0.236 g/cc, matrix tensile strength in the strongest direction=386 MPa, matrix tensile strength in the direction orthogonal to the strongest direction=218 MPa, elongation at maximum load in the strongest direction=24%, and elongation at maximum load in the direction orthogonal to the strongest direction=38.1%. The percent weight of the fluoroelastomer within the composite material was about 74%.

This membrane was imbibed with the fluoroelastomer described previously in this example. The fluoroelastomer was dissolved in PF5080 (3M, St Paul, Minn.) in an about 4% concentration. The solution was coated using a mayer bar onto the ePTFE membrane (while being supported by a polyethylene release film) and dried in a convection oven A 20 mm wide strip of the composite material was rolled into a fiber and spirally wrapped around each stent frame post 1006 on the support structure 1001 of FIG. 6. This spirally wrapped composite fiber creates a cushion member which will be located between a portion of the support structure and the leaflet to minimize stress related to direct contact between the support structure and the leaflet.

Figure 7:
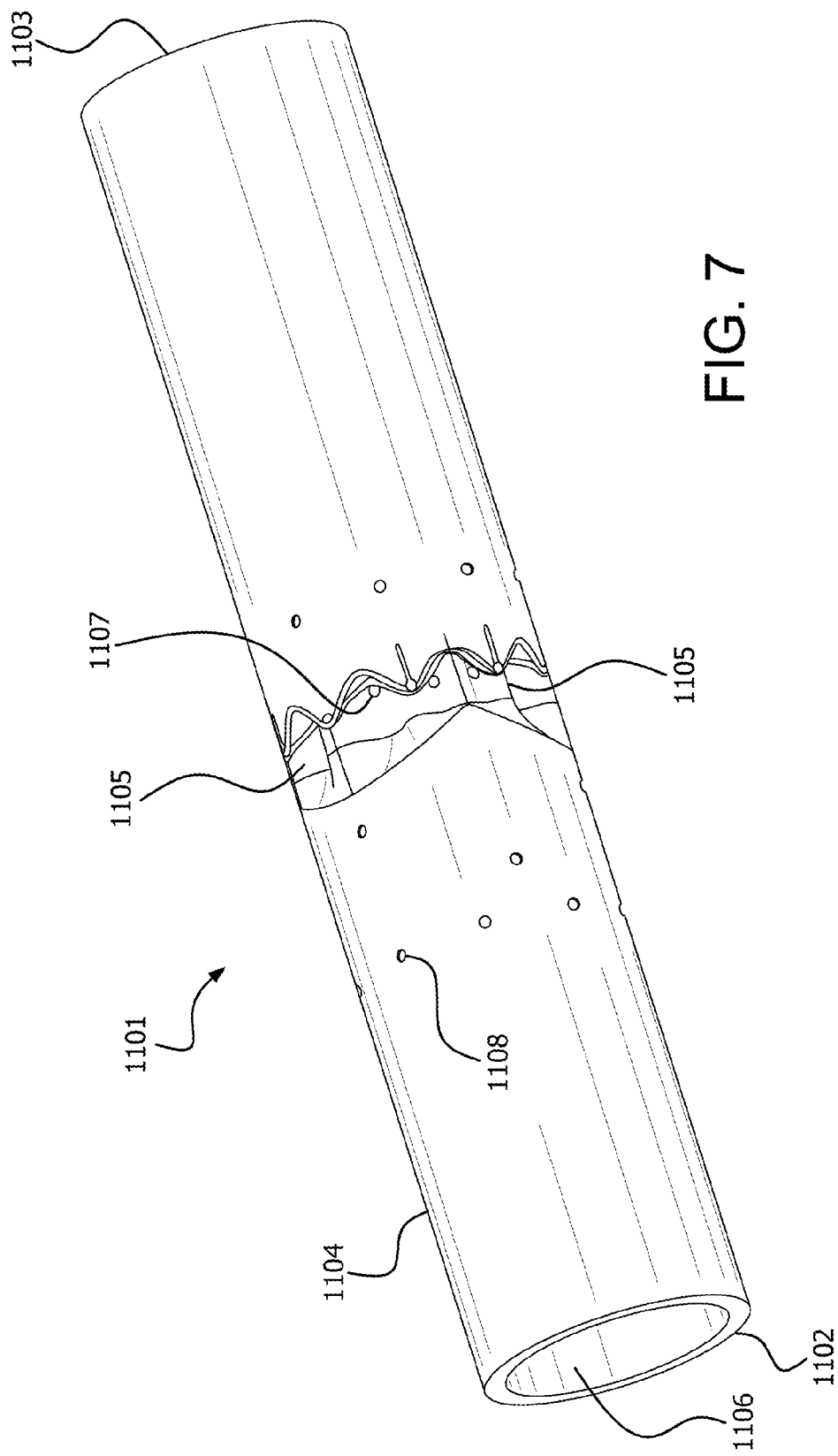
FIG. 7 is a schematic illustration of a mandrel having a generally cylindrical shape shown, in accordance with an embodiment.

A mandrel 1101 was machined from aluminum in a generally cylindrical shape shown as in FIG. 7. The mandrel 1101 contained a first end 1102 and an opposing, second end 1103. The mandrel 1101 had an outer surface 1104 having several irregular shallow pockets 1105, each generally for forming the coaptation surfaces (not shown) of a finished valve assembly (not shown).

The mandrel 1101 had forty-eight 0.5 mm diameter vent holes in the form of pocket vent holes 1107 and surface vent holes 1108. Twelve pocket vent holes 1107 were positioned at the bottom of each of the irregular shallow pockets 1105 that pass from the irregular shallow pockets 1105 to a central cavity 1106 running within the center of the mandrel 1101. Thirty-six surface vent holes 1108 were distributed across the outer surface 1104 of the mandrel 1101 that pass from the outer surface 1104 to the central cavity 1106. In a subsequent step, these pocket vent holes 1107 and surface vent holes 1108 allow for trapped air to be vented away from a valve during a molding process.

An elastomeric composite of ePTFE membrane and a fluoroelastomer was made as described hereafter. The fluoroelastomer previously described in this example was dissolved in a fluorinated solvent (Fluorinert® Electronic Liquid FC-72, 3M Inc., St. Paul, Minn.) in a ratio of 3 parts copolymer to 97 parts solvent by weight. A continuous slot die coating process operating at a line speed of approximately 1.8 m/min and a solution coating rate of approximately 96 g/min was utilized to imbibe this solution into an ePTFE membrane that was fed from a roll.

A biaxially expanded ePTFE membrane that had not been amorphously locked, and having the following properties was used: thickness=0.0025 mm, density=0.236 g/cc, matrix tensile strength in the strongest direction=386 MPa, matrix tensile strength in the direction orthogonal to the strongest direction=218 MPa, elongation at maximum load in the strongest direction=24%, and elongation at maximum load in the direction orthogonal to the strongest direction=38.1%.

The imbibed ePTFE membrane was restrained in the clamps of a heated, uniaxial tenter frame where the length direction corresponded with the strongest direction of the membrane, and fed into a 2.4 m long heated chamber.

The rails of the tenter frame were positioned to accommodate a 100 mm wide imbibed ePTFE membrane entering the heated chamber, enabling the heated composite to shrink due to the application of heat so that it exited the chamber with an approximate 56 mm width. The line speed was set to provide a dwell time of about 45 seconds within the heated chamber and the material reached a maximum temperature of approximately 180° C., thereby driving off substantially all of the fluorosolvent.

Figure 5:
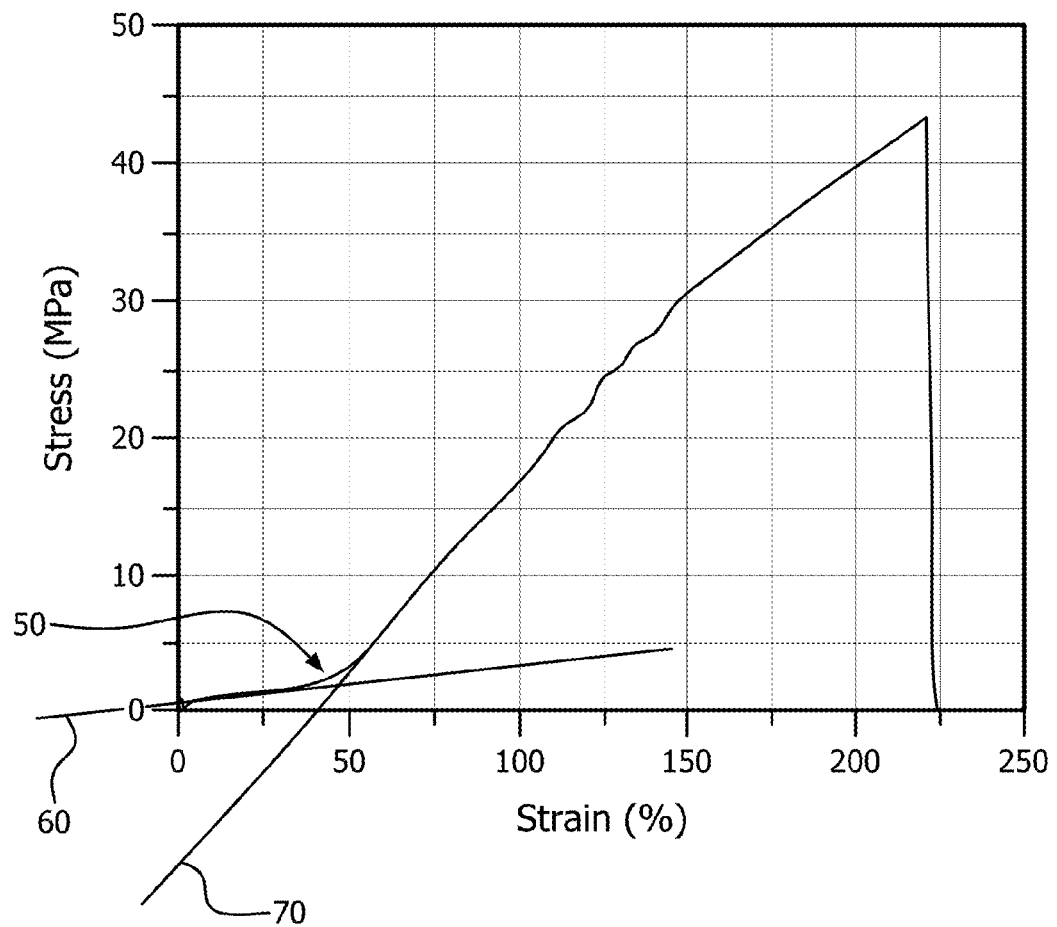
FIG. 5 is a graphical illustration of stress versus strain of a composite in the direction orthogonal to the strongest direction according to an embodiment where the intersection of tangent lines depicts a stop point of the composite, in accordance with an embodiment.

This imbibing process enabled the copolymer to at least partially penetrate the pores of the membrane and to create a coating of the copolymer on the surface of the membrane The stress of this elastomeric composite was about 43 MPa. The stress-strain curve is shown as FIG. 5 with stress plotted against strain. The stress-strain curve 111 exhibits an inflection point due to the change in slope upon reaching an elongation referred to herein as the stop point 112. In FIG. 5, the intersection of two tangent lines depicts the stop point 112 of the composite material, which is about 45%. The intersection of the tangent lines is depicted by intersection point 50. An estimate of the stop point 112 may be determined in the following manner. The slope of the stress-strain curve 111 prior to reaching the stop point 112 can be approximated by drawing a straight line tangent to the curve as shown as first line 60 in FIG. 5. The slope of the stress-strain curve 111 beyond the stop point can be approximated by drawing a straight line tangent to the stress-strain curve 111 as shown as second line 70 in FIG. 5. The strain corresponding to the intersection of the two tangent lines is an estimation of the stop point 112 for that composite material. It is to be understood that this same technique can be applied to stress-strain curves of other materials, such as membranes and leaflets, of embodiments presented herein.

Four layers of this elastomeric composite were wrapped circumferentially around the mandrel 1101. The elastomeric composite was pierced using sharp pointed tweezers above each of the 48 vent holes.

Figure 8:
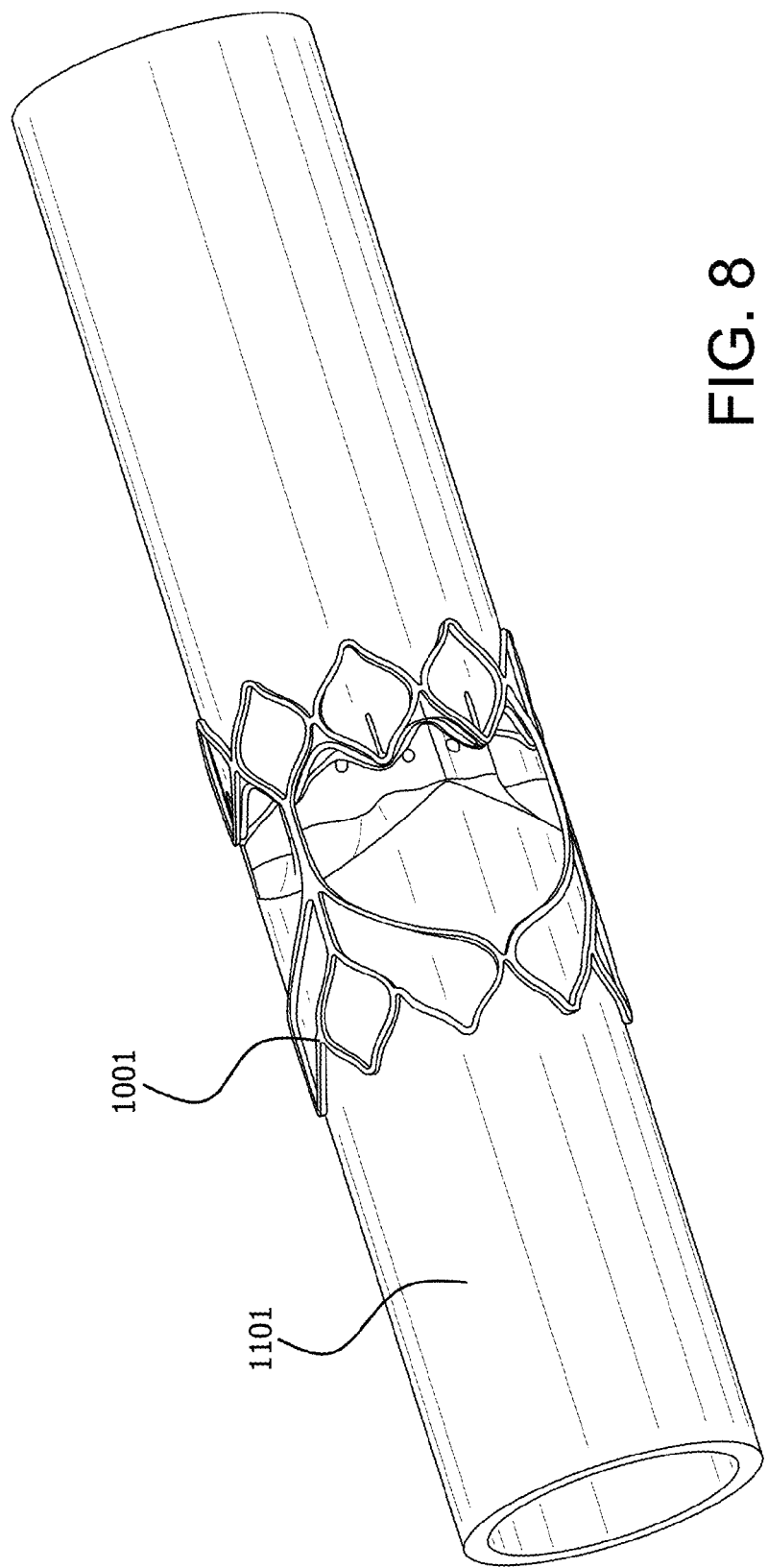
FIG. 8 is a schematic illustration of depicting the position of the support structure on the mandrel, in accordance with an embodiment.

The support structure 1001, which is a metallic balloon expandable structure, with composite fiber wrapped posts was slid over the elastomeric composite and mandrel 1101 and was positioned as shown in FIG. 8.

A 0.025 mm thick film of the fluoroelastomer previously described was obtained. A 3 mm wide strip of this fluoroelastomer film was positioned on top of the leaflet closed cells 1004 of the support structure 1001. Additional strips of fluoroelastomer film with widths of 10, 15, and 20 mm were sequentially positioned on top of each of the stent frame posts 1006. Eight additional layers of the elastomeric composite were wrapped around the mandrel 1101 and all the previously applied components.

A sacrificial composite material comprising ePTFE and polyimide with a thickness of approximately 0.004 mm was wrapped around the mandrel and previously applied components. Adhesive-backed polyimide tape was used to attach the ePTFE/polyimide composite to the mandrel at each end and to seal the longitudinal seam.

The mandrel 1102 with previously applied components was then mounted in a pressure vessel so that the central cavity 1106 was plumbed to atmosphere. The central cavity 1106 extended from the first end 1102 axially through the mandrel 1101 and communicates to the 48 previously described pocket vent holes 1107 and surface vent holes 1108.

About 414 KPa (60 psi) of helium pressure was applied to the pressure vessel, forcing the ePTFE/fluoroelastomer composite material against the mandrel 1101 and the support structure 1001. Heat was applied to the pressure vessel until the temperature inside the mandrel reached about 264° C., about 55 minutes later. The heat was removed and the pressure vessel was allowed to cool to room temperature. This process thermally bonded the layers of ePTFE/fluoroelastomer composite material to each other and to the support structure 1001. The pressure was released and the mandrel was removed from the pressure vessel. The valve assembly was slid off of the mandrel 1101 and the sacrificial ePTFE/polyimide composite material was removed.

A horizontal slit was made through the ePTFE/elastomer composite material near the upper ring of the support structure 1001. Small sheets of 0.76 mm thick FEP film were pressed against each of the three leaflets and clamped in place using hemostats so that the valve assumed a closed shape. The valve was placed in an oven at 180° C. for 15 minutes while held in this position.

After removing the FEP sheets, the valve leaflets were trimmed to their final length and excess ePTFE/elastomer composite was trimmed around the support structure, which resulted in a valve 800 as shown in FIGS. 9A and 9B showing the leaflets 802.

The performance of the leaflets 802 in this valve 800 were characterized on a real-time pulse duplicator that measured typical anatomical pressures and flows across the valve 800, generating an initial or "zero fatigue" set of data for that particular valve 800. The valve 800 was then transferred to a high-rate fatigue tester and was subjected to approximately 200 million cycles.

The flow performance was characterized by the following process:

The valve 800 was pressed into a silicone annular ring to allow the valve 800 to be subsequently evaluated in a real-time pulse duplicator.

The potted valve 800 was then placed into a real-time left heart flow pulse duplicator system. The flow pulse duplicator system included the following components supplied by VSI Vivitro Systems Inc., Victoria BC, Canada: a Super Pump, Servo Power Amplifier Part Number SPA 3891; a Super Pump Head, Part Number SPH 5891B, 38.320 cm$^2$ cylinder area; a valve station/fixture; a Wave Form Generator, TriPack Part Number TP 2001; a Sensor Interface, Part Number VB 2004; a Sensor Amplifier Component, Part Number AM 9991; and a Square Wave Electro Magnetic Flow Meter, Carolina Medical Electronics Inc., East Bend, N.C., USA.

In general, the flow pulse duplicator system uses a fixed displacement, piston pump to produce a desired fluid flow through the valve 800 under test.

The heart flow pulse duplicator system was adjusted to produce the desired flow, mean pressure, and simulated pulse rate. The valve 800 under test was then cycled for about 5 to 20 minutes.

Pressure and flow data were measured and collected during the test period, including ventricular pressures, aortic pressures, flow rates, and pump piston position.

The valve 800 in this example had a pressure drop of 5.2 mm Hg, EOA of 2.97 and regurgitant fraction of 14.4%

The durability of the leaflets 802 in this example were evaluated in a high rate fatigue tester (Six Position Heart Valve Durability Tester, Part Number M6 was supplied by Dynatek, Galena, Mo.) and was driven by a Dynatek Dalta DC 7000 Controller. This high rate fatigue tester displaces fluid through a valve 800 with a typical cycle rate of about 780 cycles per minute. During the test, the valve 800 can be visually examined using a tuned strobe light. The leaflets 802 were tested to 200 million cycles with no visible signs of holes, tears, or delamination in the leaflets 802.

Figure 2:
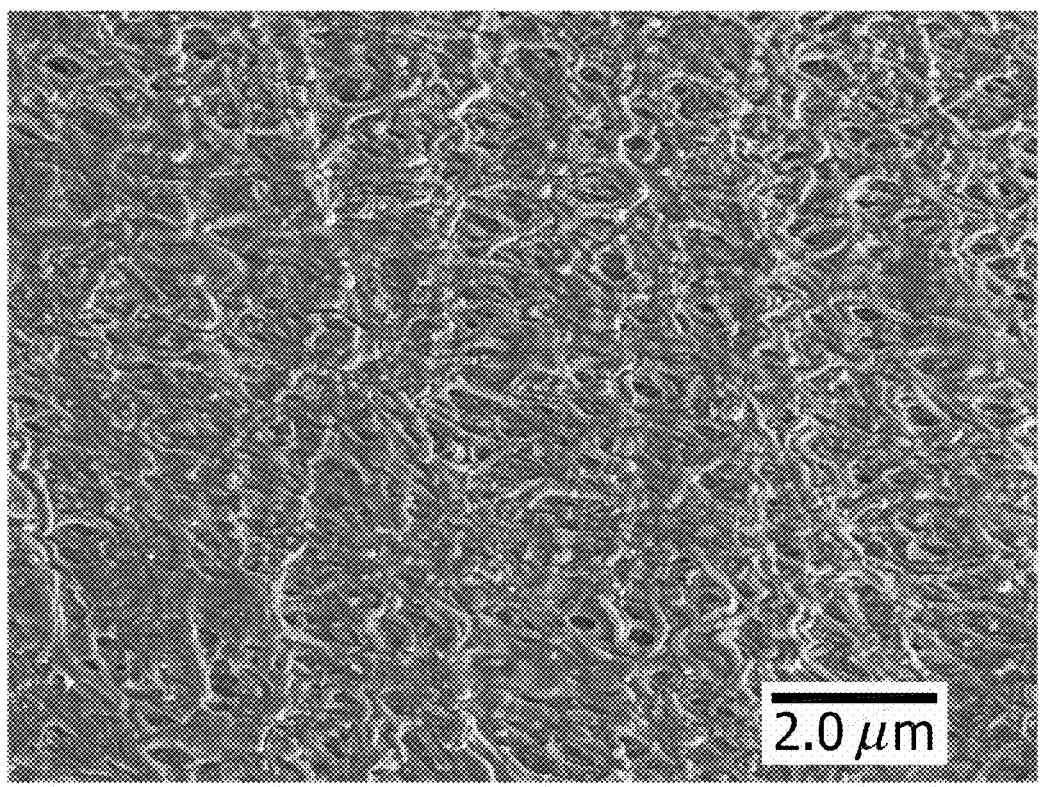
FIG. 2 is a scanning electron micrograph (SEM) of the surface of a leaflet with the fluoroelastomer removed taken at 10000×, in accordance with an embodiment.

One of the leaflets 802 was cut from the support structure 1001. The elastomer was removed as described in the test method set forth above. It is noted that the elastomer does not need to be fully removed from the leaflet 802 to reveal the serpentine fibrils. FIG. 2 is an SEM of the surface of the leaflet 802 taken at 10,000× magnification. The leaflet 802 was stretched 23% from the relaxed length so as to open the structure to more clearly see the fibrils. A sufficient amount of elastomer was removed to reveal the presence of serpentine fibrils, that is, fibrils extending in a serpentine shape.

Figure 4:
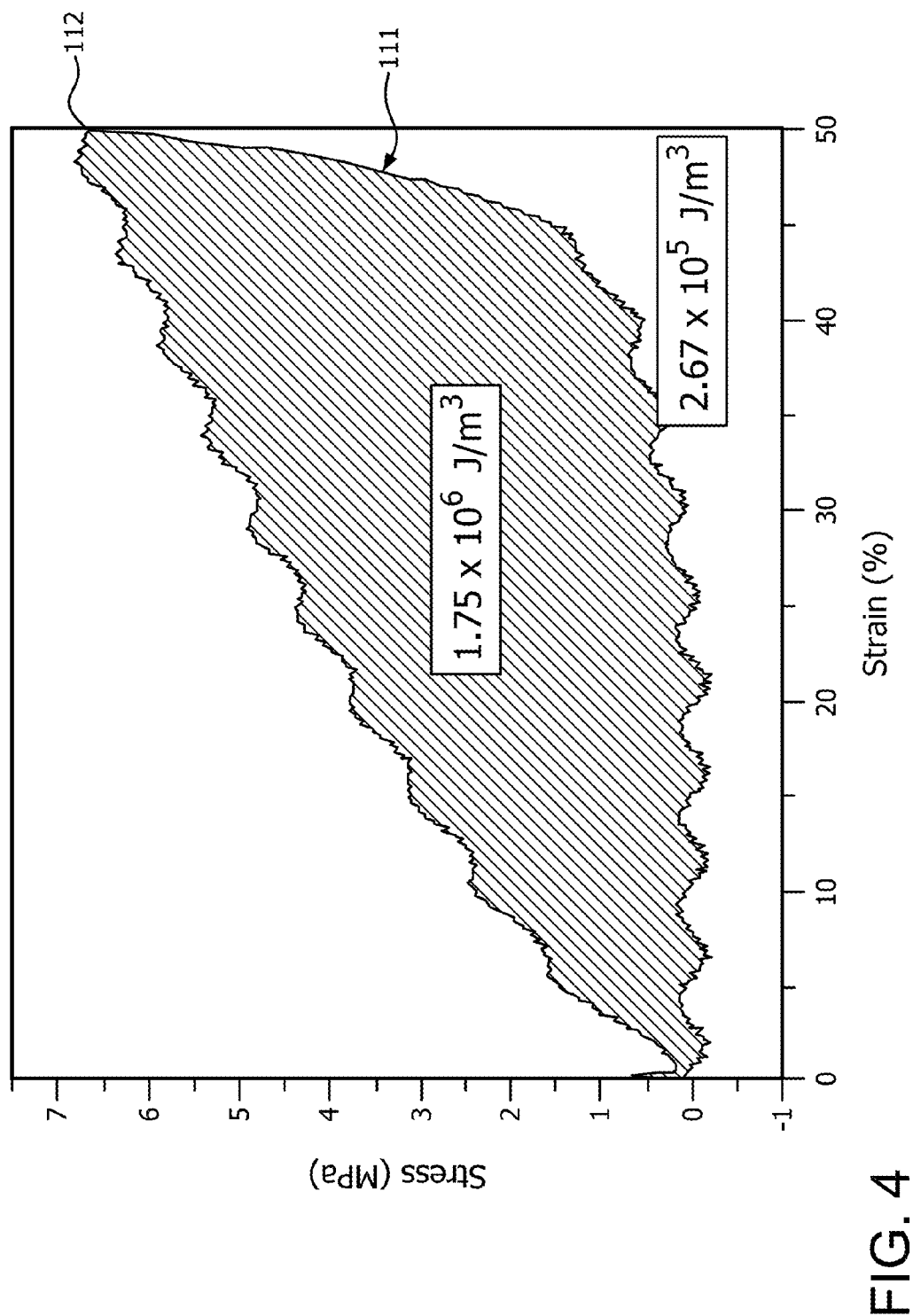
FIG. 4 is graphical illustration of the percent unrecoverable strain energy density of the sample made in accordance with Example 1, in accordance with an embodiment.

The percent unrecoverable strain energy density of the leaflet 802 was determined to be about 86.6% and is depicted by the area bound by the elongation and return curves in FIG. 4, which indicated the elastic property of the leaflet 802. In addition, it was determined that the leaflet 802 had an ultimate tensile strength of about 53 MPa.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. A prosthetic valve, comprising:
a leaflet formed of at least one layer comprising a composite material including at least one expanded fluoropolymer membrane having serpentine fibrils and the at least one expanded fluoropolymer membrane being imbibed with an elastomer, wherein the at least one expanded fluoropolymer membrane is a retracted fluoropolymer membrane, wherein the serpentine fibrils are free of wrinkles when in a retracted state.

2. The prosthetic valve of claim 1, wherein the expanded fluoropolymer membrane comprises a plurality of pores and the elastomer is present in substantially all of the pores.

3. The prosthetic valve of claim 1, wherein the fluoropolymer is polytetrafluoroethylene.

4. The prosthetic valve of claim 1, wherein the leaflet has a ratio of thickness (μm) to number of layers of the composite material of less than about 5.

5. The prosthetic valve of claim 1, wherein the composite material is substantially free of wrinkles.

6. The prosthetic valve of claim 1, wherein the expanded fluoropolymer membrane comprises a microstructure of substantially only serpentine fibrils.

7. The prosthetic valve of claim 1, wherein elastic properties are present in an axial direction of the leaflet.

8. The prosthetic valve of claim 1, wherein the elastomer is selected from the group consisting of perfluoromethylvinyl ether-tetrafluoroethylene copolymers, perfluoro (alkyl vinyl ether)-tetrafluoroethylene copolymers, silicones and polyurethanes.

9. The prosthetic valve of claim 1, wherein the leaflet is operatively coupled to a support structure and is movable between closed and open configurations relative to the support structure.

10. A prosthetic valve, comprising:
a leaflet able to be cycled between a closed configuration to substantially prevent blood flow through the prosthetic valve and an open configuration to allow blood flow through the prosthetic valve, the leaflet including at least one layer comprising a composite material including at least one expanded fluoropolymer membrane having serpentine fibrils and an elastomer, wherein the at least one expanded fluoropolymer membrane is a retracted fluoropolymer membrane, wherein the serpentine fibrils are free of wrinkles when in a retracted state, wherein the expanded fluoropolymer membrane comprises a plurality of pores and the elastomer is present in substantially all of the pores.

11. The prosthetic valve of claim 10, wherein the composite material is substantially free of wrinkles.

12. The prosthetic valve of claim 10, wherein the fluoropolymer is polytetrafluoroethylene.

13. The prosthetic valve of claim 10, wherein the expanded fluoropolymer membrane comprises a microstructure of substantially only serpentine fibrils.

14. The prosthetic valve of claim 10, wherein the leaflet is operatively coupled to a support structure and is movable between the closed and open configurations relative to the support structure.

15. The prosthetic valve of claim 10, wherein the leaflet has a ratio of thickness (μm) to number of layers of the composite material of less than about 5.

16. The prosthetic valve of claim 10, wherein elastic properties are present in an axial direction of the leaflet.

17. The prosthetic valve of claim 10, wherein the elastomer is selected from the group consisting of perfluoromethylvinyl ether-tetrafluoroethylene copolymers, perfluoro (alkyl vinyl ether)-tetrafluoroethylene copolymers, silicones and polyurethanes.

18. A prosthetic valve, comprising:
a support structure; and
a leaflet formed of at least one layer comprising a composite material including at least one expanded fluoropolymer membrane having serpentine fibrils and the at least one expanded fluoropolymer membrane being imbibed with an elastomer, wherein the at least one expanded fluoropolymer membrane is a retracted fluoropolymer membrane, wherein the serpentine fibrils are free of wrinkles when in a retracted state, wherein the leaflet is movable between a closed configuration and an open configuration relative to the support structure, and
wherein the leaflet is able to be cycled between the closed configuration to substantially prevent blood flow through the prosthetic valve and the open configuration to allow blood flow through the prosthetic valve.

19. The prosthetic valve of claim 18, wherein the expanded fluoropolymer membrane comprises a plurality of pores and the elastomer is present in substantially all of the pores.

20. The prosthetic valve of claim 18, wherein the composite material is substantially free of wrinkles.

21. The prosthetic valve of claim 18, wherein the fluoropolymer is polytetrafluoroethylene.

22. The prosthetic valve of claim 18, wherein the expanded fluoropolymer membrane comprises a microstructure of substantially only serpentine fibrils.

23. The prosthetic valve of claim 18, wherein elastic properties are present in an axial direction of the leaflet.

24. The prosthetic valve of claim 18, wherein the elastomer is selected from the group consisting of perfluoromethylvinyl ether-tetrafluoroethylene copolymers, perfluoro (alkyl vinyl ether)-tetrafluoroethylene copolymers, silicones and polyurethanes.

25. A prosthetic valve, comprising:
a leaflet formed of at least one layer comprising a composite material exhibiting an increase in stiffness when elongated to at least about 30% strain, the composite material including at least one expanded fluoropolymer membrane having serpentine fibrils and the at least one expanded fluoropolymer membrane being imbibed with an elastomer, wherein the at least one expanded fluoropolymer membrane is a retracted fluoropolymer membrane, wherein the serpentine fibrils are free of wrinkles when in a retracted state.

26. The prosthetic valve of claim 25, wherein the composite material exhibits an increase in stiffness when elongated to at least about 40% strain.

27. The prosthetic valve of claim 25, wherein the composite material exhibits an increase in stiffness when elongated to at least about 45% strain.

28. The prosthetic valve of claim 25, wherein the composite material exhibits an increase in stiffness when elongated to at least about 50% strain.

29. The prosthetic valve of claim 25, wherein the expanded fluoropolymer membrane comprises a microstructure of substantially only serpentine fibrils.

30. The prosthetic valve of claim 25, wherein the expanded fluoropolymer membrane comprises a plurality of pores and the elastomer is present in substantially all of the pores.

31. The prosthetic valve of claim 25, wherein the fluoropolymer is polytetrafluoroethylene.

32. The prosthetic valve of claim 25, wherein the leaflet has a ratio of thickness (μm) to number of layers of the composite material of less than about 5.

33. The prosthetic valve of claim 25, wherein the composite material is substantially free of wrinkles.

34. The prosthetic valve of claim 25, wherein elastic properties are present in an axial direction of the leaflet.

35. The prosthetic valve of claim 25, wherein the elastomer is selected from the group consisting of perfluoromethylvinyl ether-tetrafluoroethylene copolymers, perfluoro (alkyl vinyl ether)-tetrafluoroethylene copolymers, silicones and polyurethanes.

36. The prosthetic valve of claim 25, wherein the leaflet is operatively coupled to a support structure and is movable between closed and open configurations relative to the support structure.

37. A prosthetic valve, comprising:
a leaflet able to be cycled between a closed configuration to substantially prevent blood flow through the prosthetic valve and an open configuration to allow blood flow through the prosthetic valve, the leaflet including at least one layer comprising a composite material exhibiting an increase in stiffness when elongated to at least about 30% strain, the composite material including at least one expanded fluoropolymer membrane and an elastomer, wherein the expanded fluoropolymer membrane comprises a plurality of pores and the elastomer is present in substantially all of the pores, wherein the at least one expanded fluoropolymer membrane is a retracted fluoropolymer membrane, wherein the serpentine fibrils are free of wrinkles when in a retracted state.

38. The prosthetic valve of claim 37, wherein the composite material is substantially free of wrinkles.

39. The prosthetic valve of claim 37, wherein the fluoropolymer is polytetrafluoroethylene.

40. The prosthetic valve of claim 37, wherein the at least one expanded fluoropolymer membrane comprises serpentine fibrils.

41. The prosthetic valve of claim 37, wherein the expanded fluoropolymer membrane comprises a microstructure of substantially only serpentine fibrils.

42. The prosthetic valve of claim 37, wherein the expanded fluoropolymer membrane comprises a plurality of serpentine fibrils.

43. The prosthetic valve of claim 37, wherein the leaflet is operatively coupled to a support structure and is movable between the closed and open configurations relative to the support structure.

44. A prosthetic valve, comprising:
a support structure; and
a leaflet formed of at least one layer comprising a composite material exhibiting an increase in stiffness when elongated to at least about 30% strain, the composite material including at least one expanded fluoropolymer membrane and the at least one expanded fluoropolymer membrane being imbibed with an elastomer, wherein the at least one expanded fluoropolymer membrane is a retracted fluoropolymer membrane, wherein the serpentine fibrils are free of wrinkles when in a retracted state,
wherein the leaflet is movable between closed and open configurations relative to the support structure, and
wherein the leaflet is able to be cycled between the closed configuration to substantially prevent blood flow through the prosthetic valve and the open configuration to allow blood flow through the prosthetic valve.

45. The prosthetic valve of claim 44, wherein the expanded fluoropolymer membrane comprises a plurality of pores and the elastomer is present in substantially all of the pores.

46. The prosthetic valve of claim 44, wherein the composite material is substantially free of wrinkles.

47. The prosthetic valve of claim 44, wherein the fluoropolymer is polytetrafluoroethylene.

48. The prosthetic valve of claim 44, wherein the at least one expanded fluoropolymer membrane comprises serpentine fibrils.

49. The prosthetic valve of claim 44, wherein the expanded fluoropolymer membrane comprises a microstructure of substantially only serpentine fibrils.

50. The prosthetic valve of claim 44, wherein the expanded fluoropolymer membrane comprises a plurality of serpentine fibrils.

51. The prosthetic valve of claim 44, wherein elastic properties are present in an axial direction of the leaflet.

52. The prosthetic valve of claim 44, wherein the elastomer is selected from the group consisting of perfluoromethylvinyl ether-tetrafluoroethylene copolymers, perfluoro (alkyl vinyl ether)-tetrafluoroethylene copolymers, silicones and polyurethanes.

* * * * *